United States Patent
Rubin

(10) Patent No.: US 6,655,527 B1
(45) Date of Patent: Dec. 2, 2003

(54) KIT FOR REMOVING MILDEW

(75) Inventor: Lynn J. Rubin, Atlantic Beach, NC (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 41 days.

(21) Appl. No.: 10/115,820

(22) Filed: Apr. 3, 2002

Related U.S. Application Data

(60) Provisional application No. 60/304,483, filed on Jul. 12, 2001.

(51) Int. Cl.[7] .............................................. B65D 69/00
(52) U.S. Cl. ........................ 206/229; 206/223; 206/568
(58) Field of Search ................................ 206/219, 222, 206/223, 229, 232, 361, 362, 568, 576; 222/129; 401/123, 125; 134/6

(56) References Cited

U.S. PATENT DOCUMENTS

| | | | | |
|---|---|---|---|---|
| 3,558,497 A | * | 1/1971 | Lawes | 510/309 |
| 3,655,096 A | * | 4/1972 | Easter | 222/82 |
| 3,684,723 A | * | 8/1972 | Best et al. | 510/316 |
| 4,917,238 A | * | 4/1990 | Schumacher | 206/223 |
| 4,975,109 A |  | 12/1990 | Friedman et al. | |
| 5,035,321 A | * | 7/1991 | Denton | 206/225 |
| 5,256,182 A |  | 10/1993 | Friedman et al. | |
| 5,545,349 A |  | 8/1996 | Kurii et al. | |
| 5,567,247 A |  | 10/1996 | Hawes et al. | |
| 5,605,578 A |  | 2/1997 | Hawes et al. | |
| 5,783,550 A |  | 7/1998 | Kuriyama et al. | |
| 6,129,096 A | * | 10/2000 | Johnson | 134/34 |
| 6,135,276 A | * | 10/2000 | French et al. | 206/225 |
| 6,159,391 A |  | 12/2000 | Kobayashi et al. | |
| 6,235,124 B1 |  | 5/2001 | Rubin | |
| 6,302,608 B1 | * | 10/2001 | Holmes et al. | 401/125 |

FOREIGN PATENT DOCUMENTS

GB    1 252 298    * 11/1971

OTHER PUBLICATIONS

Military Specifications for MIL–D–16791G, pp. 1–19, Jan. 1990.

\* cited by examiner

*Primary Examiner*—David T. Fidei
(74) *Attorney, Agent, or Firm*—Mark O. Glut

(57) ABSTRACT

The kit for removing mildew includes a premeasured amount of sodium perborate and a premeasured amount of non-ionic detergent. The premeasured amount of sodium perborate, the premeasured amount of non-ionic detergent and water combine to form an aqueous solution that can be applied to a mildew infected area. The aqueous solution removes mildew from a mildew infected area.

3 Claims, 1 Drawing Sheet

KIT FOR REMOVING MILDEW

CROSS-REFERENCE TO RELATED APPLICATIONS

Figure 1:
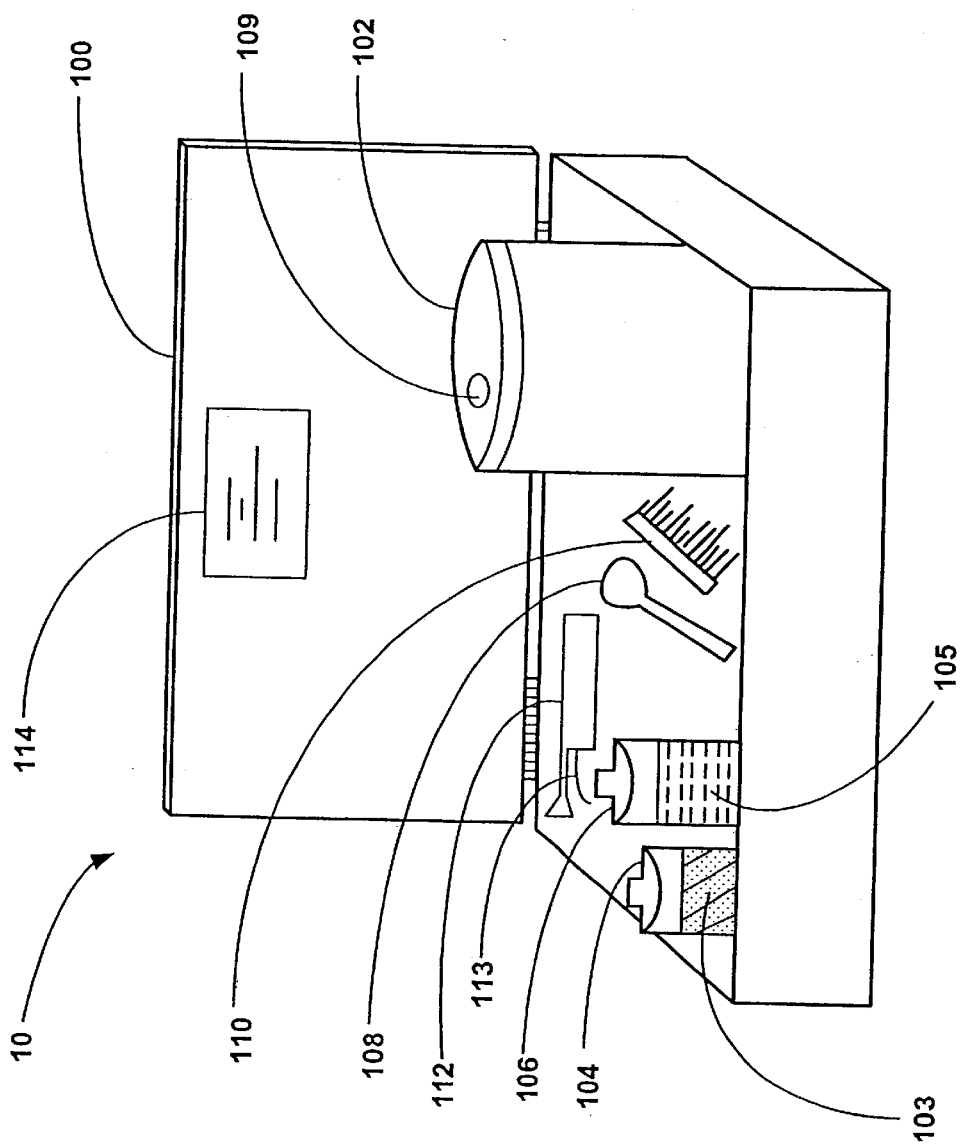

This application claims the benefit under 35 U.S.C. section 119(e) of Provisional Application 60/304,483 filed on Jul. 12, 2001.

The above listed invention is hereby cross-referenced and related to U.S. Pat. No. 6,235,124 issued May 22, 2001, entitled "Method and Solution for Removal of Mildew" by inventor Lynn J. Rubin. U.S. Pat. No. 6,235,124 is not admitted to be prior art with respect to the present invention. The patent is hereby incorporated by reference. Both inventions are assigned to the same assignee and have been invented by the same inventor.

STATEMENT OF GOVERNMENT INTEREST

The invention described herein may be manufactured and used by or for the Government of the United States of America for governmental purposes without payment of any royalties thereon or therefor.

BACKGROUND

The present invention relates to a kit for removing mildew. More specifically, but without limitation, the present invention relates to a kit for removing mildew from aircraft.

The damaging effects of mildew are well known throughout the scientific and non-scientific community. Mildew growth on interior surfaces of aircraft, particularly military aircraft, has been a chronic problem, especially when these aircraft are operated in humid climates. Excess buildup of mildew can cause corrosion as well as operational damage to aircraft. Mildew can also cause accelerated degradation of paint and decals. Mildew buildup is also a health hazard to pilots and maintenance personnel. Buildup of mildew causes unpleasant odors and can be demoralizing to pilots, maintenance personnel and passengers.

Most methods of mildew removal have proven to be extremely time consuming, labor intensive and often inadequate. Solutions that adequately removed mildew in the past have caused accelerated corrosion to the aircraft structural metals as well as to the aircraft. Other solutions, such as ones containing sodium hypochlorite (chlorine bleach), are damaging to the environment and may only bleach the mildew stain and not remove it. Certain solutions require many ingredients, which are difficult, potentially dangerous, and time consuming to prepare and use. Other solutions are expensive as well as difficult and dangerous to store. A method for removal of mildew from aircraft that solved these problems is described in U.S. Pat. No. 6,235,124, which is assigned to the same assignee of the present invention and invented by the same inventor and, as stated previously, hereby incorporated by reference.

U.S. Pat. No. 6,235,124 teaches the user of the method to prepare an aqueous solution with sodium perborate and a non-ionic detergent. Testing has found that once this solution is prepared it is no longer an effective mildew remover after 8 hours. Therefore, the solution must be prepared and then used as soon as possible. Thus there exists the need for a system or a kit for preparing the solution and then immediately applying the solution to a mildew infected area. There is also a need for a kit for mildew removal wherein the cleaning solution may be simply prepared in a non-laboratory environment, such as on an airfield, a factory, a yard or aboard a ship, and prepared by an unskilled laborer, layperson or an apprentice sailor, soldier or airman easily and quickly.

For the foregoing reasons, there is a need for a kit for removing mildew.

SUMMARY

The present invention is directed to a kit for removing mildew that meets the needs enumerated above and below.

The present invention is directed to a kit for removing mildew, which comprises of a premeasured amount of sodium perborate and a premeasured amount of non-ionic detergent. The premeasured amount of sodium perborate, the premeasured amount of non-ionic detergent and water combine to form an aqueous solution that can be applied to a mildew infected area. Upon application and rinsing, the aqueous solution removes mildew from a mildew infected area.

It is an object of the present invention to provide a kit for removing mildew that is inexpensive, easy to store and environmentally friendly. Sodium perborate is a colorless, free flowing granular chemical that is easy to store and use. The resultant solution decomposes into water, oxygen and sodium borate.

It is also an object of the invention to provide a kit for removing mildew that utilizes a mildew removing system that is non-corrosive to aluminum, steel and aircraft structural materials. The resultant solution may actually inhibit corrosion by passivating metal surfaces and increasing the life of various materials. The solution and method may also possibly delay the growth of mildew on aircraft. The kit for removing mildew may also be used to effectively remove mildew from cars, trucks, trains, ships, buildings or any other object that needs removal of mildew.

It is a further object of the invention to provide a kit for removing mildew, which provides mildew cleaning, bleaching, and stain removal. The resultant solution also works to enhance removal of common operational oils and soils as well as the removal of mildew.

It is also an object of the present invention to provide a kit for removing mildew, wherein the resultant solution breaks down protein channels within the fungus (mildew), thus eliminating its presence, not just bleaching the stain.

It is also an object of the invention to reduce cleaning time of aircraft. Current methods require significant cleaning time and can cause delays in having the aircraft available for use. The present invention has been shown to decrease cleaning time.

It is also an object of the invention to provide for a kit for removing mildew wherein the mildew removing solution may be simply prepared in a non-laboratory environment, and prepared by an unskilled laborer or an apprentice sailor, soldier or airman easily and quickly.

DRAWINGS

These and other features, aspects and advantages of the present invention will become better understood with reference to the following description and appended claims, and accompanying drawing wherein:

FIG. 1 is a perspective view of one of the preferred embodiments of the kit for removing mildew.

DESCRIPTION

One of the preferred embodiments of the present invention is illustrated by way of example in FIG. 1. As shown in FIG. 1, the kit for removing mildew 10 includes a premeasured amount of sodium perborate 103, and a premeasured amount of non-ionic detergent 105.

The premeasured amount of sodium perborate 103 may be stored in a sodium perborate container 104. A container is defined, but without limitation, as anything that can contain or hold something, a compartment, a receptacle, a carton, a box, a bag, or any apparatus that can store something and prevent it from spilling or falling out of the apparatus. A container typically may have a cap or opening to allow the contents to be poured out or removed from the container. In a preferred embodiment, the sodium perborate 103 may be stored in a sealed foil bag that may be ripped open, and then the empty foil bag can be discarded. The sealed foil bag may have a small cutout so that the foil bag may be easily opened. The premeasured amount of sodium perborate 103 may be in powder form. The sodium perborate container 104 may be manufactured from plastic, metal, metal alloy, aluminum foil, or any type of material that lends itself to the manufacture of a container that would safely and effectively store sodium perborate.

The premeasured amount of non-ionic detergent 105 may be stored in a detergent container 106. The detergent container 106 may be manufactured from plastic, metal, metal alloy, aluminum foil, or any type of material that lends itself to the manufacture of a container that would safely and effectively store a non-ionic detergent. In a preferred embodiment, the sodium perborate 103 may be stored in a sealed foil bag that may be ripped open.

The premeasured amount of non-ionic detergent 105 can be any detergent conforming to military specification MIL-D-16791G (incorporated herein by reference) or equivalent. The premeasured amount of non-ionic detergent 105 can be in liquid form, and a non-ionic surface-active agent containing a minimum of 99% active ingredient. Some examples, but without limitation, of the types of detergents that can be used are alkyl aryl polyether alcohol (alkyl phenol ether of polyethylene glycol) type where the alkyl group is iso-octyl or isononyl, or the linear alkyl polyether alcohol (alkyl ether of polyethylene glycol) type where the alkyl group is linear primary or secondary alkyl. However, any type of naturally occurring or synthetic detergents or surfactants can be used.

The kit for removing mildew 10 may also contain a large high-density polyethylene (HDPE) or polypropylene mixing container 102 for mixing the premeasured amount of sodium perborate 103, the premeasured amount of non-ionic detergent 105 and water. The mixing container 102 may be a large open ended or partially open ended container, drum, bottle, tank, jug, carboy, can, tub, pail, urn, jar, or the like. The mixing container 102 may have a cap or lid to cover the opening. When the sodium perborate, the non-ionic detergent and water are mixed they form an aqueous solution that can effectively clean and remove mildew.

The kit for removing mildew 10 may also include an agitator 108 to mix and agitate the solution. An agitator 108 is any devise, system or apparatus that can shake, move the ingredients briskly or mix the ingredients. The agitator 108 could be, but without limitation, a large spoon, ladle, scoop, mixer, stirrer, dipper, stick or the like. If the mixing container 102 has a lid, the mixing container 102 (with the prepared aqueous solution within the mixing container 102) can be shaken to properly agitate the aqueous solution.

The agitator 108 may be an automated agitator utilizing mechanical and/or electrical devices to properly agitate the aqueous solution. The agitator 108 may be, but without limitation, an automatic fan stirrer, an automated shaker, a robot agitator, a drill with an agitation bit attached, or the like. The agitator 108 may also be, but without limitation, an air-powered mixer, an electric mixer, a direct drive mixer, a gear drive mixer, a single propeller mixer, a dual propeller mixer, or any other type of agitator or mixer. It is understood, however, any type of mechanical, electrical, or any combination thereof, agitator or agitation process can be utilized where practicable.

The kit for removing mildew 10 may also contain a solution applicator. The solution applicator is any devise, system or apparatus that can apply the mixed aqueous solution to a mildew infected area. The solution applicator can be an applicator, but without limitation, selected from the group of a spray bottle, a chemical wash bottle with a dispensing nozzle, a compression sprayer, a conventional sprayer, a nylon brush 110 and cheesecloth. When using a spray bottle the solution may be poured into the spray bottle and sprayed on the mildew infected area. As shown in FIG. 1, the applicator may be a drum or pail pump 112 for dispensing and transferring the aqueous solution from the mixing container 102 onto the mildew infected area.

The mixing container 102 may have a corresponding aperture 109 that allows the pump 112 to draw the aqueous solution out of the mixing container 102 and then apply the solution to the mildew infected area. The pump 112 may be a manual pump or a powered pump. The manual pump may be, but without limitation, a siphon, plunger, piston, rotary or diaphragm type pump, or the like. The powered pump may be electric powered or air powered. The pump 112 may have a flexible discharge hose 113 or spout with the ability to spray the solution on the mildew infected area. Specifically, the pump 112 may be a polyethylene pump, which is made to withstand liquids like detergents, alkalies and solvents. As seen in FIG. 1, in a preferred embodiment, the kit for removing mildew 10 contains a pump 112 for applying the aqueous solution and a brush 110 for scrubbing the aqueous solution once it is applied to the mildew infected area. The brush 110 may have screw-in handle to allow the user to scrub without bending over. The screw-in handle would allow an extension to be attached to the brush 110 so that hard to reach areas may be accessed with the brush 110.

The kit for removing mildew 10 may also include a kit container 100. The kit container 100 can be a housing that can hold or store all the items of the kit for removing mildew 10. Within the kit container 100 there may be component fasteners which fasten each item of the kit for removing mildew 10 to the inside of the kit container 100. In one of the embodiments, the mixing container 102 may also serve as the kit container 100. All the items would be placed in the mixing container 102 and the mixing container 102 may contain a lid in order to keep all the items safely stored inside the mixing container 102 during transport or storage of the kit 10.

For moderately mildew infected surfaces or large size jobs, such as the H-46 helicopter, the kit for removing mildew 10 may have approximately ten (10) ounces (by weight) of sodium perborate, approximately two and a half fluid ounces of non-ionic detergent, and a substantially five (5) gallon-mixing container. For more significantly mildew infected surfaces or larger size jobs, such as the H-53 and H-60 helicopters, the approximate ratios would be doubled. For other size jobs, the appropriate ratios are about 1–2% by weight of sodium perborate and about one-half of a fluid ounce of non-ionic detergent to every gallon of water.

For optimal performance the mixed solution should be at least greater than about 77 degrees Fahrenheit. The preferred temperature of the mixed solution is in the range of about 90 to about 110 degrees F. This can be accomplished by adding heated or warm water. The mixed solution has a preferred pH between about 9.5 and about 10.0.

The kit for removing mildew 10 can also include a set of instructions 114 on how to use the kit 10 to remove mildew from a mildew infected area. These instructions 114 could include the method described in U.S. Pat. No. 6,235,124. Specifically, the preferred instructions for a preferred embodiment of the invention could state: (1.) empty container of premeasured sodium perborate into the mixing container; (2.) empty container of premeasured non-ionic detergent into the mixing container; (3.) add warm water (the appropriate amount of water would be indicated based on the size of the premeasured sodium perborate and premeasured non-ionic detergent), the temperature of the water being at least 77 degrees Fahrenheit, preferably in the range of about 90 to about 110 degrees F.; (4.) agitate or mix the solution with the agitator; (5.) apply agitated solution to mildew infected area with the applicator, during use keep solution agitated by agitating or mixing the solution about every 1 to 3 minutes; (6.) for best results leave the solution on the mildew infected area for about five to ten minutes, then, if needed, scrub the mildew infected area, preferably with a nylon brush; (7.) rinse the solution from the mildew infected area, for best results rinse with pressurized water having a pressure in a range from about 50 to about 80 psi.

When introducing elements of the present invention or the preferred embodiment(s) thereof, the articles "a", "an", "the" and "said" are intended to mean there are one or more of the elements. The terms "comprising," "including," and "having" are intended to be inclusive and mean that there may be additional elements other than the listed elements.

Although the present invention has been described in considerable detail with reference to certain preferred versions thereof, other versions are possible. Therefore, the spirit and scope of the appended claims should not be limited to the description of the preferred versions contained herein.

What is claimed is:

1. A kit for removing mildew, comprising:
   a.) a premeasured amount of sodium perborate, the sodium perborate being in powder form;
   b.) a premeasured amount of non-ionic detergent, the non-ionic detergent being in liquid form, the non-ionic detergent being a detergent selected from the group of alkyl aryl polyether alcohol, linear alkyl polyether alcohol, and synthetic detergent;
   c.) a mixing container for mixing the premeasured amount of sodium perborate and the premeasured amount of non-ionic detergent and a premeasured amount of water, the premeasured amount of sodium perborate, the premeasured amount of non-ionic detergent and the premeasured amount of water combine to form an aqueous solution that can be applied to a mildew infected area, the aqueous solution removes mildew from the mildew infected area, the mixing container is a polypropylene nixing container, wherein the premeasured amount of sodium perborate is about 1–2% by weight, the premeasured amount of non-ionic detergent is about one half of a fluid ounce to every gallon of water;
   d.) an applicator for applying the aqueous solution to the mildew infected area, the applicator being a pump, the pump is a plunger pump with a flexible discharge spout, the pump further being a polyethylene pump;
   e.) an agitator for mixing the aqueous solution;
   f.) a brush for scrubbing the mildew infected area once the aqueous solution is applied; and,
   g.) a kit container for storing the premeasured amount of sodium perborate, the premeasured amount of non-ionic detergent, the mixing container, the applicator, the agitator, and the brush.

2. A kit for removing mildew, comprising:
   a.) a premeasured amount of sodium perborate, the sodium perborate being in powder form;
   b.) a premeasured amount of non-ionic detergent, the non-ionic detergent being in liquid form, the non-ionic detergent being a detergent selected from the group of alkyl aryl polyether alcohol, linear alkyl polyether alcohol, and synthetic detergent;
   c.) a mixing container for mixing the premeasured amount of sodium perborate and the premeasured amount of non-ionic detergent and a premeasured amount of water, the premeasured amount of sodium perborate, the premeasured amount of non-ionic detergent and the premeasured amount of water combine to form an aqueous solution that can be applied to a mildew infected area, the aqueous solution removes mildew from the mildew infected area, the mixing container is a polypropylene mixing container, wherein the premeasured amount of sodium perborate is about 10 ounces by weight, the premeasured amount of non-ionic detergent is about two and a half fluid ounces, and the container is a substantially five gallon container;
   d.) an applicator for applying the aqueous solution to the mildew infected area, the applicator being a pump, tire pump is a plunger pump with a flexible discharge spout, the pump further being a polyethylene pump;
   e.) an agitator for mixing the aqueous solution;
   f.) a brush for scrubbing the mildew infected area once the aqueous solution is applied; and,
   g.) a kit container for storing the premeasured amount of sodium perborate, the premeasured amount of non-ionic detergent, the mixing container, the applicator, the agitator, and the brush.

3. A kit for removing mildew, comprising:
   a.) a premeasured amount of sodium perborate, the sodium perborate being in powder form;
   b.) a premeasured amount of non-ionic detergent, the non-ionic detergent being in liquid form, the non-ionic detergent being a detergent selected from the group of alkyl aryl polyether alcohol, linear alkyl polyether alcohol, and synthetic detergent;
   c.) a mixing container for mixing the premeasured amount of sodium perborate and the premeasured amount of non-ionic detergent and a premeasured amount of water, the premeasured. amount of sodium perborate, the premeasured amount of non-ionic detergent and the premeasured amount of water combine to form an aqueous solution that can be applied to a mildew infected area, the aqueous solution removes mildew from the mildew infected area, the mixing container is a polypropylene mixing container, wherein the premeasured amount of sodium perborate is about 20 ounces by weight, the premeasured amount of non-ionic detergent is about 5 fluid ounces, and the container is a substantially ten gallon container;
   d.) an applicator for applying the aqueous solution to the mildew infected area, the applicator being a pump, the pump is a plunger pump with a flexible discharge spout, the pump further being a polyethylene pump;
   e.) an agitator for mixing the aqueous solution;
   f.) a brush for scrubbing the mildew infected area once the aqueous solution is applied; and,
   g.) a kit container for storing the premeasured amount of sodium perborate, the premeasured amount of non-ionic detergent, the mixing container, the applicator, the agitator, and the brush.

* * * * *

UNITED STATES PATENT AND TRADEMARK OFFICE
CERTIFICATE OF CORRECTION

PATENT NO. : 6,655,527 B1 Page 1 of 1
DATED : December 2, 2003
INVENTOR(S) : Lynn J. Rubin It is certified that error appears in the above-identified patent and that said Letters Patent is hereby corrected as shown below:

<u>Column 5,</u>
Line 42, should read -- a polypropylene mixing container, wherein the premea- --

<u>Column 6,</u>
Line 18, should read -- mildew infected area, the applicator being a pump, the --
Line 40, should read -- water, the premeasured amount of sodium perborate, --

Signed and Sealed this

Tenth Day of February, 2004

JON W. DUDAS
*Acting Director of the United States Patent and Trademark Office*